United States Patent [19]

Carlson

[11] Patent Number: 4,547,323

[45] Date of Patent: Oct. 15, 1985

[54] SYNTHESIS OF 2,2-DIMETHYL-4-METHYLENEGLUTARIC ACID AND DERIVATIVES

[75] Inventor: Gary M. Carlson, North Olmsted, Ohio

[73] Assignee: SCM Corporation, New York, N.Y.

[21] Appl. No.: 591,803

[22] Filed: Mar. 21, 1984

[51] Int. Cl.$^4$ ............... C07C 120/00; C07C 121/00; C07C 69/593; C07C 67/465; C07C 51/353; C07C 57/13

[52] U.S. Cl. ............... 260/465.4; 560/190; 560/193; 560/196; 560/198; 560/202; 562/595

[58] Field of Search ............... 560/202, 190, 193, 196, 560/198; 562/595; 260/465.4

[56] References Cited

U.S. PATENT DOCUMENTS

| | | | |
|---|---|---|---|
| 2,232,785 | 2/1941 | Howk | 560/202 X |
| 3,074,999 | 1/1963 | Rauhut et al. | 560/202 |
| 3,227,745 | 1/1965 | McClure | 560/202 |
| 3,322,819 | 5/1967 | Schreyer | 560/202 X |

*Primary Examiner*—Natalie Trousof
*Assistant Examiner*—Vera C. Clarke
*Attorney, Agent, or Firm*—Thomas M. Schmitz

[57] ABSTRACT

The process comprises dimerizing methacrylic acid derivatives in the presence of an organic Co(II) glyoxime to produce 2,2-dimethyl-4-methyleneglutaric acid and/or derivatives thereof. Methacrylic acid derivatives include methacrylic acid or derivatives of methacrylic acid. The composition produced by the process comprises a glutaric dimer acid which can be further polymerized to form high molecular weight polymer useful as a binder in protective coatings.

18 Claims, No Drawings

SYNTHESIS OF 2,2-DIMETHYL-4-METHYLENEGLUTARIC ACID AND DERIVATIVES

BACKGROUND OF THE INVENTION

This invention pertains to the dimerization of methacrylic acid derivatives and more particularly to the dimerization of methacrylic acid and methacrylic acid derivatives in the presence of an organic Co(II) catalyst to produce 2,2-dimethyl-4-methyleneglutaric acid derivatives.

The importance of difunctional materials in the synthesis of useful polymeric materials is well known. Diols and diacids are used in the production of polyesters. Difunctional isocyanates are used for the production of polyurethanes and for the crosslinking of polyfunctional resins. Diepoxides are widely used for a variety of coating materials or as crosslinkers for acid functional materials. One method of preparing a new class of difunctional materials is through the dimerization of monofunctional methacrylic acid derivatives carrying the desired functionality.

The 2,2-dimethyl-4-methyleneglutaric acid derivatives have been synthesized previously in low yield as side reactions. For instance, carbonylation of allene in water in the presence of ruthenium catalysts produced methacrylic acid as well as some methyleneglutarate derivative (J. Org. Chem., 26, 3126, 1961). Similarly, base catalyzed (sodium alkoxide) oligomerization of vinyl monomers produced low yields of alpha-methylene glutaric acid derivatives according to *European Polymer Journal*, Vol. 7, pages 1435–1443 (1971). Thermal initiated methyl methacrylate oligomer apparently produces minor yields of cyclic dimers and linear trimers thereof as suggested in *European Polymer Journal*, Vol. 16, pages 785–791 (1980). All of the disclosed methods, however, produce very low yields and are unacceptable for commercial processes. A recent publication has suggested the use of cobalt porphyrin complex as a catalyst for chain transfer to monomer generally for producing oligomers and polymers, as disclosed in J. Poly. Chem., Ed., Vol. 19, 877 (1981).

It now has been found that 2,2-dimethyl-4-methyleneglutaric acid and derivatives thereof can be synthezied by dimerization of a methacrylic monomer in the presence of an organic Cobalt(II) catalyst in a free radical process to produce a predominately dimerized product comprising 2,2-dimethyl-4-methyleneglutaric acid (2,2,4-DMMG) and derivatives thereof. The process provides an excellent improvement over prior art methods of controlling the dimerization of methacrylic monomers. In accordance with this invention, the Co(II) catalyst effectively functions as a catalyst to effect a free radical dimerization of methacrylic monomers to produce the dimer. The resulting DMMG derivative can be used as a diacid for reaction with glycols to produce polyesters exhibiting good hydrolysis resistance and the ability to produce air-dry tack-free surface. Polymers produced from the DMMG derivatives are generally useful as binders in protective coatings. Glutaric acid derivative dimers produced in accordance with the process of this invention resulted in yields of between 60% and 80% or more based on the methacrylate monomer conversion to dimer. These and other advantages of this invention will become more apparent by referring to the detailed description of the invention and the illustrative examples.

SUMMARY OF THE INVENTION

Briefly, the process comprises dimerizing a methacrylic acid derivative comprising methacrylic acid or a methacrylic acid derivative in the presence of organic Co(II) complex to produce 2,2-dimethyl-4-methyleneglutaric acid and derivatives thereof.

DETAILED DESCRIPTION OF THE INVENTION

The process and composition of this invention pertains to the dimerization of a methacrylic monomer in the presence of a Co(II) organic catalyst to produce a dimer of methacrylic acid or a glutaric acid derivative.

Referring first to methacrylic monomers, the monomers are generally illustrated by the structure:

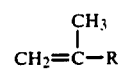

where R represents any functionality not interfering with the catalytic ability of the catalyst complex. These functionalities can include esters, including alkyl, aryl, alkylisocyanate, hydroxyalkyl, aminoalkyl, haloalkyl, aminoalkylamides, methacrylic acid and its acid salts, and other derivatives of methacrylic acid including methacrylonitrile, methacrolein, methacrylamine, and 2-(2-propenyl)-oxazoline.

Methacrylic acid derivatives are ethylenically unsaturated monomers such as lower alkyl esters of methacrylic acid having an alkyl ester portion containing between 1 to 22 carbon atoms as well as aromatic derivatives of acrylic and methacrylic acid. Useful monomers include, for example, methacrylic acid, methyl methacrylate, ethyl methacrylate, butyl methacrylate, propyl methacrylate, 2-ethyl hexyl methacrylate, cyclohexyl methacrylate, decyl methacrylate, isodecyl methacrylate, benzyl methacrylate, and various reaction products such as butyl, phenyl, and cresyl glycidyl esters reacted with methacrylic acids, hydroxyl alkyl methacrylates, such as hydroxyethyl and hydroxypropyl methacrylates, as well as amino methacrylates, 2-isocyanatoethyl methacrylate, and glycidyl methacrylate, N,N-dimethyl-3-propyl methacrylamide, methacrylamide, dimethyl amino ethyl methacrylate.

Referring next to the organic cobalt(II) catalyst complex, the Co(II) catalyst comprises an organic complex derivative such as Co(II) dimethylgloxime pyridine, or Co(II)-mesotetraphenylporphyrin. In accordance with this invention, Co(II) catalyst should be used in amounts of at least about 0.001% and preferably between 0.001% and 0.01% based on the weight of methacrylate monomer subjected to dimerization. The catalyst surprisingly controls the reaction to produce dimers of the starting monomers. The catalyst can be any of the class of materials which function as catalysts for chain transfer to monomer in free radical polymerizations. These can include porphyrin derivatives such as mesotetraphenylporphyrin or cobalt(II) complexes of dioximes. The dioxime can be any 1,2- or 1,3-dioxime such as, but not limited to the dioximes derived from 2,3-butanedione, 2,3-hexanedione, 2,4-heptanedione, 2,5-dimethyl-3, 4-hexanedione, 3-methyl-2-, 4-hexanedione, 1,2-cyclohexanedione, 3-phenyl-2, 4-pentanedione, 2-naphthylglyoxal or camphoroquinone. Additionally, the dioxime can be derived from an aromatic dione such as, but not limited to, 4-chloro-1,2-benzoquinone, 1,2-napthoquinone, 3,7-dimethyl-1-, 2-napthoquinone, 3-chloro-1, 2-napthoquinone or substituted 1,2-anthraquinones. A basic ligand can also be used to modify the catalyst. These basic ligands can be materials such as pyridine, triphenylphosphine or imidazole derivatives.

In accordance with the process of this invention, methacrylic monomer can be dimerized by reacting the methacrylic derivative monomer in the presence of the Co(II) organic complex catalyst and non-reactive solvent, if desired, and free radical initiator at temperatures between 0° C. and 150° C. and preferably above 50° C. for thermal initiation. Photochemical initiation can be below 50° C. and as low as 0° if desired. Reflux temperatures for monomer mixture ordinarily are desirable. Preferred polymerization catalysts are azo catalysts such as azodiisobutyronitrile and dimethylazodiisobutyrate. After reacting the methacrylic monomers together for 1 to 6 hours at temperatures between 50° C. and 95° C., the monomer conversion to dimer is between 60% to 80% by weight. The molecular weights of the dimers typically are between 150 and 450, and for higher molecular weight methacrylate monomers, the molecular weight of the dimer can be as high as 1,000.

Batch polymerizations can be carried out in a nitrogen flushed reactor under a nitrogren flow. Preferably, the polymerization is carried out in the absence of oxygen or under nitrogen blanket to avoid undesirable interference of oxygen with the Co(II) catalyst. The monomer, solvent, and initiator can then be charged to the reactor. The catalyst can be formed in situ by the addition of ligand and cobalt (II) acetate tetrahydrate or chloride hexahydrate. Semi-continuous polymerizations can be carried out in a reactor equipped with a stirrer (mechanical or magnetic), thermometer, condenser, and nitrogen inlet. Solvent was charged to the reactor and flushed thoroughly with nitrogen during upheat to reflux. The initiator and monomer solution was added dropwise over approximately 2 hours. The dimer formed in the early stages of reaction is known to undergo side reactions leading to decreased yields at higher conversions. Improved yields can be obtained using a continuous process in which a monomer, catalyst, and free radical initiator solution is heated and allowed to react to low conversions. Removal of product and recirculation of monomer and catalyst result in improved yields.

Numerous derivatives have potential use in the coatings field as well as other applications. These include dimers of glycidyl methacrylate, hydroxyethylmethacrylate, hydroxypropylmethacrylate, methacrylonitrile, isocyanatoethylmethacrylate, meta-2-isocyanato-2-propyl-methylstyrene (m-TMI), butyl methacrylate, methacrylamide, and 2-isopropenyloxazoline.

The methacrylic dimer can be reacted with glycols to form polyesters containing reactive double bonds which can be further copolymerized with conventional monomer such as styrene. Typical glycols include for instance, ethylene glycol, propylene glycol, dipropylene glycol, diethylene glycol, butylene glycols, as well as high molecular weight glycol. Esterification can be by bulk polymerization at temperatures above about 175° C. Dicarboxylic acids are often used in polyesters and can include, for instance, phthalic anhydride, isophthalic acid, adipic acid, succinic acids, maleic acid, fumaric acid, itaconic, and similar saturated or unsaturated dicarboxylic acid. Monomers can include styrene, methyl styrene, and similar alkyl or alkyl substituted styrenes, vinyl acetate, and acrylates such as methyl methacrylate.

The merits and advantages of this invention are further illustrated by the following examples.

EXAMPLE 1

Semi-Continuous Process for DMMG Synthesis

Methylmethacrylate (MMA), 100 g., and azobisisobutyronitrile (AIBN) 1 g., were charged to a 500 ml flask and thoroughly flushed with nitrogen. Cobalt(II) acetate hexahydrate, 0.138 g. and dimethylglyoxime, 0.183 g., were added followed by 0.30 ml of pyridine. The temperature was raised to 90° C. in 30 minutes and a solution of 2.0 g. AIBN in 200 ml of MMA added over one hour. Following completion of the monomer addition, the solution was held for one hour at which time AIBN, 0.075 g., was added. The solution was held at 90° C. and cooled. Analysis indicated 82 percent conversion of monomer to a product containing 64 percent of the desired dimer, DMMG. The DMMG is easily purified by fractional distillation.

EXAMPLE 2

Semi-Continuous Process for DMMG Synthesis

A process substantially similar to Example 1 with a three hour monomer addition. Analysis of the final material indicated 80% conversion of monomer to a product containing 63% DMMG. The additional material being comprised substantially of trimer and tetramers of MMA.

EXAMPLE 3

Batch Charged Dimerization of Methyl Methacrylate

Methyl methacrylate (MMA), 1500 g. and ethyl acetate, 1500 g., were charged to a 5 l. flask and thoroughly flushed with nitrogen. Cobalt(II) acetate hexahydrate, 0.44 g., AIBN, 15 g., dimethylglyoxime, 0.38 g., and pyridine, 6 ml., were added. The solution was heated to reflux and held for approximately 2 hours. The crude DMMG was distilled through a packed column at 74.2° C. at 1.7 mm., removing an appreciable forecut containing predominantly MMA monomer. A total of 677 G. DMMG was isolated, with a purity of 95%.

EXAMPLE 4

Dimerization of Butyl Methacrylate

To a 1 l. flask was charged 300 g. of butylmethacrylate (BMA) and 300 g., of methylethylketone (MEK). The flask was flushed throughly with nitrogen and 0.09 g. of cobalt(II) acetate hexahydrate and 0.08 g. of dimethylglyoxime was added followed by 1.6 ml of pyridine. Ethyl acetate, 80 ml., was then added to aid the dissolution of the catalyst. The solution was heated to 80° C. and held for 3.75 hours. The final material contained 19.5% unreacted BMA. The product contained 66% BMA dimer along with 34% higher oligomers.

EXAMPLE 5

Dimerization of Glycidyl Methacrylate

MEK, 150 g., was charged to a 500 ml flask and flushed thoroughly with nitrogen. Cobalt(II) acetate hexahydrate, 0.044 g., dimethylglyoxime, 0.040 g., and pyridine, 1 ml., were added. The temperature was increased to 80 degrees C. and solution of 1.5 g of AIBN in 150 g. glycidylmethacrylate added over 4 hours. The solution was held at 80° C. for 1 hour and 0.5 g of AIBN added. Analysis of the final material indicated a monomer conversion of 89% to a product containing 30% of GMA dimer. The remaining 70% of products were higher oligomers of GMA. This dimer is a difunctional epoxy and useful in a wide variety of applications.

EXAMPLE 6

Dimerization of Hydroxyethylmethacrylate

In a procedure substantially similar to Example 5, hydroxyethylmethacrylate (HEMA) was dimerized to give a final product which represented a 83% conversion of monomer to product containing 54% dimerized HEMA along with higher oligomers.

EXAMPLE 7

Dimerization of Methyl Methacrylate

MMA, 100 ml., was charged to a 500 ml flask and flushed thoroughly with nitrogen. Cobalt (II) acetate hexahydrate, 0.138 g., and dimethylglyoxime, 0.179 g., were added followed by 0.30 ml of pyridine. The temperature was raised to 70° C. at which point a solution of 2 g. AIBN in 200 ml MMA was added dropwise over a period of 3 hours. Following completion of the addition an additional portion of AIBN, 0.75 g., was added. Following an additional hold period of 1 hour, the final sample was 38% converted to a product containing 80% of the dimer.

EXAMPLE 8

Dimerization of Methacrylic Acid

MEK, 200 g., and 1.1 g. of Co(II)-mesotetraphenylporphyrin were charged to a 500 ml flask and thoroughly flushed with nitrogen. The temperature was raised to 78° C. and a solution of 70 g MMA, and 0.7 g AIBN in 100 g. MEK was added over a period of 5 hours. After 1 hour of addition the yield of methacrylic acid dimer was 48%. The yield decreased during the addition due to limited solubility of the catalyst in the methacrylic acid/MEK solution.

EXAMPLE 9

Dimerization of Methyl Methacrylate Catalyzed by Co-mesotetraphenylporphyrin

Cobalt(II)-mesotetraphenylporphyrin, 0.5 g., and 200 g of MEK was added to a 500 ml flask. After flushing thoroughly with nitrogen, the solution was heated to 80° C. A solution of 2.0 g AIBN in MMA was added over 3 hours. Analysis of the final product indicated 39% yield of dimer based on the monomer converted.

EXAMPLE 10

In a process similar to Example 5, 1050 g of MEK was charged to a 5000 ml flask. Following through flushing with nitrogen, 0.294 grams of Co(II) chloride hexahydrate, 0.280 grams of DMG, and 24.7 ml of a 0.1N solution of potassium hydroxide in methanol. The solution was heated to 70° C. and a solution of 20 g AIBN in 2000 g MMA added over 2 hours.

I claim:

1. A process for producing a low molecular weight 2,2-dimethyl-4-methyleneglutaric acid derivative, comprising: dimerizing a methacrylate monomer in the presence of a free radical initiator and in the presence of between 0.001% and 0.1% Cobalt(II) complex catalyst for chain transfer to monomer based on the weight of said monomer to produce a product comprising a 2,2-dimethyl-4-methyleneglutaric acid derivative, wherein said catalyst is a Cobalt(II) dioxime or Cobalt(II) porphyrin catalyst.

2. The process in claim 1 wherein the product comprises at least about 50% dimer by weight.

3. The process in claim 1 wherein the methacrylate monomer comprises a derivative of methacrylic acid.

4. The process in claim 1 wherein the methacrylate comprises methacrylic acid.

5. The process in claim 1 where the methacrylate comprises methyl methacrylate.

6. The process in claim 1 wherein the cobalt(II) catalyst is cobalt(II) dimethylglyoxime pyridine.

7. The process in claim 1 wherein the cobalt catalyst is a cobalt(II) alkyl dioxime complex.

8. The process in claim 1 wherein the cobalt catalyst is a cobalt(II) aryl dioxime complex.

9. The process in claim 1 wherein the cobalt catalyst is a porphrin derivative complex.

10. The process in claim 1 where the methacrylate comprises 2-isocyanatoethyl methacrylate.

11. The process in claim 1 where the methacrylate comprises glycidyl methacrylate.

12. The process in claim 1 where the methacrylate comprises hydroxyethyl or hydroxypropyl methacrylate.

13. A composition comprising a 2,2-dimethyl-4-methyleneglutaric acid diester wherein said ester group is selected from the group consisting of isocyanatoalkyl, hydroxyalkyl, dialkylaminoalkyl, glycidyl, and cycloalkyl radicals.

14. A composition according to claim 13 wherein the diester is di(hydroxyethyl)2,2-dimethyl-4-methyleneglutarate.

15. A composition according to claim 13 wherein the diester is di(isocyanoethyl)2,2-dimethyl-4-methyleneglutarate.

16. A composition according to claim 13 wherein the diester is di(glycidyl)2,2-dimethyl-4methyleneglutarate.

17. A composition according to claim 13 wherein the diester is di(cyclohexyl)2,2-dimethyl-4-methyleneglutarate.

18. A composition according to claim 13 wherein the diester is di(hydroxypropyl)2,2-dimethyl-4-methyleneglutarate.

* * * * *